(12) United States Patent
Dunfee et al.

(10) Patent No.: US 7,867,769 B2
(45) Date of Patent: Jan. 11, 2011

(54) CLOG DETECTION IN A CLINICAL SAMPLING PIPETTE

(75) Inventors: William David Dunfee, Newark, DE (US); Mark Henry Sprenkle, Newark, DE (US)

(73) Assignee: Siemens Healthcare Diagnostics Inc., Deerfield, IL (US)

(*) Notice: Subject to any disclaimer, the term of this patent is extended or adjusted under 35 U.S.C. 154(b) by 547 days.

(21) Appl. No.: 11/857,922

(22) Filed: Sep. 19, 2007

(65) Prior Publication Data
US 2009/0075386 A1 Mar. 19, 2009

(51) Int. Cl.
*G01N 35/08* (2006.01)
*G01F 23/00* (2006.01)
*G01F 17/00* (2006.01)
*G01N 1/10* (2006.01)
*G01N 11/00* (2006.01)
*G01M 3/04* (2006.01)

(52) U.S. Cl. .......................... 436/54; 436/180; 436/50; 221/10; 702/55; 73/37; 73/40

(58) Field of Classification Search .................... 436/54
See application file for complete search history.

(56) References Cited

U.S. PATENT DOCUMENTS

| | | | |
|---|---|---|---|
| 5,451,373 A | 9/1995 | Lewis et al. | |
| 5,463,895 A | 11/1995 | Brentz | |
| 5,503,036 A | 4/1996 | Nguyen et al. | |
| 5,540,081 A | 7/1996 | Takeda et al. | |
| 5,562,104 A | 10/1996 | Hochberg et al. | |
| 5,622,869 A | 4/1997 | Lewis et al. | |
| 5,814,275 A | 9/1998 | Lewis et al. | |
| 5,915,282 A | 6/1999 | Merriam et al. | |
| 6,022,747 A | 2/2000 | Gherson et al. | |
| 6,060,320 A | 5/2000 | Dorenkott et al. | |
| 6,283,719 B1 | 9/2001 | Frantz et al. | |
| 6,370,942 B1 | 4/2002 | Dunfee et al. | |
| 6,938,504 B2* | 9/2005 | Camenisch | 73/864.01 |
| 7,477,997 B2* | 1/2009 | Kaplit | 702/55 |
| 2007/0025882 A1* | 2/2007 | Zuppiger et al. | 422/100 |

* cited by examiner

*Primary Examiner*—Jill Warden
*Assistant Examiner*—Jennifer Wecker
(74) *Attorney, Agent, or Firm*—Leland K. Jordan (57) ABSTRACT

Analyzing the pressure profile generated during a predetermined period of time prior to the end of an aspiration or dispensing process and comparing a pressure reading to predetermined values to determine if the aspiration or dispensing pipette was free of clogs.

10 Claims, 9 Drawing Sheets

CLOG DETECTION IN A CLINICAL SAMPLING PIPETTE

FIELD OF THE INVENTION

The present invention relates to the transfer of an amount of liquid from one container to another, and more particularly, to an improved method for ascertaining the integrity of a liquid aspiration process using a vacuum actuated pipette.

BACKGROUND OF THE INVENTION

Fully automated diagnostic analyzers are commercially available to perform chemical assays and immunoassays of biological fluids such as urine, blood serum, plasma, cerebrospinal liquids and the like. Reactions between an analyte in a patient sample and reagents used during the assay generate a signal from which the concentration of analyte in the patient sample may be calculated. Such automated analyzers typically use a sampling pipette probe or needle, to aspirate and transfer desired volumes of sample or reagent between sample containers, reagent containers and reaction cuvettes disposed on the analyzer. Hereinafter, variations of the term aspirate refers to all of such processes for extracting liquid from one container and depositing at least some of the liquid into the same or another container and further includes the supporting devices required to complete the liquid handling operations.

Aspirators typically comprise an elongated, needle-like probe or pipette having a hollow passage whereby liquid may be aspirated into and/or dispensed from the probe using appropriate pumping resources. The pipette may be carried by a transport mechanism adapted to provide horizontal and vertical movement so as to enable the pipette tip to be lowered into a liquid in a reservoir for aspiration of the liquid, and for transporting the liquid to a another location where the pipette is lowered into position for dispensing the liquid. Some type of vacuum pressure activated device, such as a piston assembly, may be incorporated into the pipette to aspirate liquid into the pipette and to dispense liquid from the pipette.

It is desirable, when aspirating a liquid, to accurately determine if any abnormalities or non-uniformities within the liquid have adversely affected the overall quality of the aspiration process. Non-uniformities such as clogs or clots, bubbles, foam, insufficient volume, etc, may exist in samples, particularly when the sample is a body fluid as these are frequently a non-uniform composition. Various methods have been developed to detect the effect of such non-uniformities during the aspiration process.

U.S. Pat. No. 6,370,942 discloses an method for evaluating the quality of a liquid aspiration for undesirable events such as partial or complete clogs, or aspiration of air by employing three separate aspiration tests including a pressure difference test to verify liquid was aspirated, a pressure recovery test to check for clogs and aspiration of unwanted cells, and a pressure shape test to check for abnormalities during aspiration, such as clogs, air aspiration, density changes (due to aspiration of blood cells), etc. Three algorithms are employed, and each must produce a positive result for the sample to be released for transfer elsewhere.

U.S. Pat. No. 6,022,747 discloses a blood clot detector having a pressure transducer on an aspiration line to provide output voltage data to a microprocessor corresponding to the vacuum level during aspiration. The microprocessor integrates the vacuum readings over time during the aspiration cycle to provide a pressure integral for each test sample aspiration. A pressure integral is determined for an unclotted aspiration and is used as a reference for comparison with the pressure integrals of each test sample aspiration to determine whether a blood clot has interfered with the test sample aspiration. Acceptability of the test sample for analysis is based upon a predetermined difference between the reference pressure integral and each test sample pressure integral.

U.S. Pat. Nos. 5,814,275, 5,622,869 and 5,451,373 relate to an apparatus for detecting obstructions of a flow line. A pressure detector detects changes in pressure within a flow cavity, indicating the presence of an obstruction. A barrier is disposed near the pressure detector so that when said flow line and pressure detector expand, the rigid barrier does not expand and the pressure detector is compressed.

U.S. Pat. No. 5,540,081 relates to a pipetting apparatus provided with clot detection comprising a nozzle for aspirating a sample. A pressure sensor and a plurality of pressure difference calculating circuits obtain a pressure difference at a different pressure calculation period. A plurality of discriminating circuits each having a different discrimination threshold value determined according to each of the pressure calculation. An alarm circuit is included for outputting a clot detection alarm signal when at least one of said discriminating circuits discriminates that the obtained pressure difference exceeds the discrimination threshold value.

U.S. Pat. No. 5,503,036 relates to an obstruction detection circuit for detecting an obstruction of a sample probe of an automated fluid sample aspiration/dispensation device and a method for detecting such an obstruction. In one embodiment, the obstruction detection circuit includes a pressure sensor measuring the pressure in a fluid conduit connecting a pump and to a sample probe orifice. The pressure within the connecting fluid conduit is measured shortly after the start of the aspiration or dispensation of a sample volume by the automated fluid sample aspiration-dispensation device. The pressure within the connecting fluid conduit is again measured after the completion of the aspiration or the dispensation by the pump, and if the pressure has not returned to a predetermined range within a predetermined amount of time, an error condition is reported.

U.S. Pat. No. 5,463,895 discloses provides an apparatus and method of detecting non-homogeneity in a fluid sample, such as the presence of foam or bubbles on the surface of the sample, and/or the presence of clots on the surface or in the bulk of the sample. This method involves determining the ambient air pressure within a pipettor, aspirating air into the pipettor as the pipettor moves towards a sample in container and monitoring for a pressure change in the pipettor to indicate the surface level of the fluid in said container. The pipettor is immersed in the fluid and a volume of fluid is withdrawn from the container; pressure changes are monitored after aspiration and compared to predetermined normal aspiration pressure windows.

Liquid aspiration quality determining processes like described are not satisfactory in all instances. For example, many systems for determining the quality or integrity of an aspiration process depend on measuring differences in vacuum pressure at different pre-determined intervals during the aspiration process and comparing a vacuum pressure values to a range of predetermined satisfactory values. Other systems compare derivatives of a vacuum pressure profile to a range of predetermined satisfactory values. As the state of the art advances, aspirated sample volumes become smaller and smaller, causing pressure differential values for liquids with different viscosities become more erratic or "noisy". In addition, pressure profiles of certain higher viscosity liquids do not reach stable end-point values. Hence, there is a need for an improved method for determining the quality of a liquid aspiration process that is effective for small aspiration volumes that may contain an unwanted full or partial clog.

SUMMARY OF THE INVENTION

It is therefore an object of this invention to provide a liquid aspiration method which is capable of ascertaining the overall quality and integrity of the amount of liquid which has been aspirated into a pipette tip. Sensed aspiration pressure data used for verification of the overall quality of the aspiration process are recorded for each sample aspiration and analyzed immediately following the aspiration event. Depending upon the volume of sample to be aspirated, taking into account system geometries, pump movement and the like, the total amount of time that aspiration pressure (vacuum) must be applied to the pipette is calculated and aspiration pumping motion is stopped a corresponding number of data reads after data collection began at the onset of the aspiration cycle. The present aspiration method checks the aspiration process for undesirable events such as partial or complete clogs by analyzing the pressure profile generated during a predetermined period of time prior to the end of the aspiration vacuum pumping and calculating an average pressure reading during only this predetermined "final pumping" period of time. It has been discovered that this "final pumping" pressure reading exceeds a predetermined minimum, if and only if, the aspiration process was free of full or partial clogs. In a related, similar process, it has also been discovered that a "final pumping" pressure reading measured during dispensing of a previously aspirated sample exceeds a predetermined minimum, if and only if, the dispensing process was free of full or partial clogs.

BRIEF DESCRIPTION OF THE DRAWINGS

For a better understanding of the invention as well as other objects and further features thereof, reference is made to the following detailed description of various preferred embodiments thereof, taken in connection with the accompanying drawings wherein.

DETAILED DESCRIPTION OF THE PREFERRED EMBODIMENTS

Figure 1:
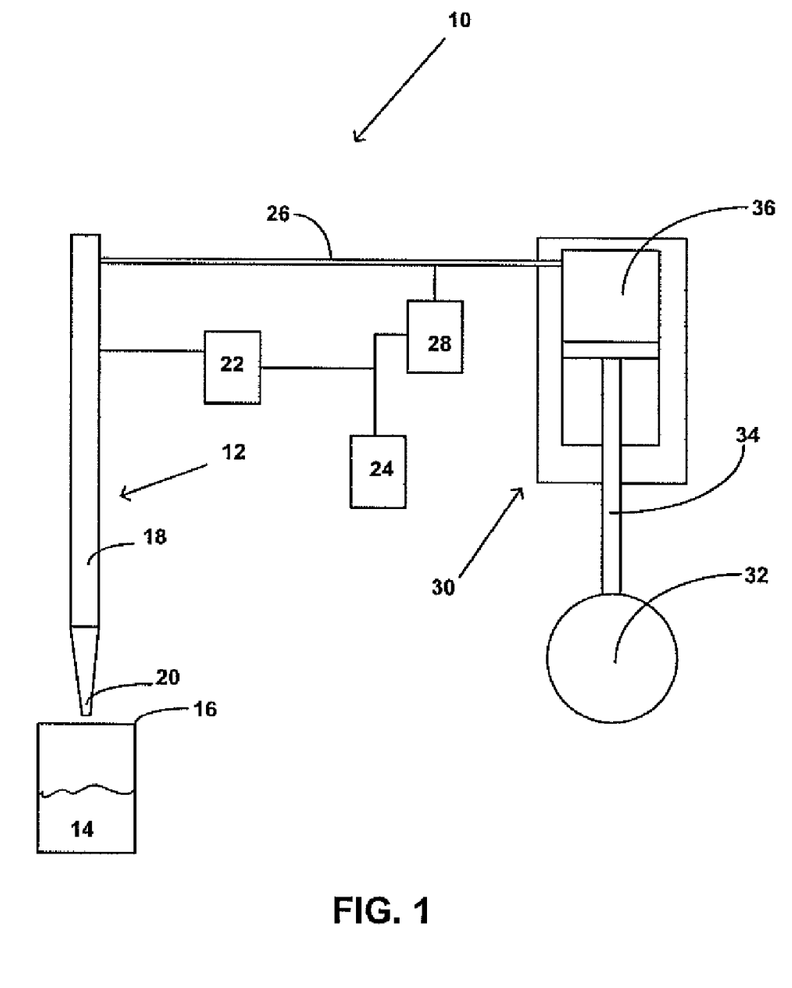
FIG. 1 is a schematic representation of an aspiration system in which the present invention may be practiced.

FIG. 1 illustrates a conventional liquid aspiration system 10 useful in practicing the present invention which includes a pipette 12 for aspirating and dispensing liquid such as a sample liquid 14 stored in a reservoir 16. Although one such sample liquid 14 is shown for the purpose of describing the liquid aspiration system 10, it will be apparent to those skilled in the art that any number of sample liquid reservoirs can be present in an automated clinical analyzer. In an exemplary embodiment, the liquid aspiration system 10 may be used in an automated clinical analyzer (not shown). Such automated clinical analyzers are well known in the art and those skilled in the art will know with certainty the functions of the elements of the analyzers to which reference is made.

Pipette 12 generally includes a central cavity 18 which may be adapted to carry a replaceable pipette tip 20 which may have a conically narrowing nose shape terminating in a distal orifice 20 through which liquid is aspirated into cavity 18, and through which liquid is dispensed therefrom. Central cavity 18 opens into the tip cavity upon engagement of the holder with the tip. Alternately, pipette tip 20 may be integral with central cavity 18. Aspiration system 10 further comprises an aspiration pressure control 30 adapted to produce a vacuum pressure within cavity 18 during aspiration and a positive pressure during dispensing. Pressure source 30 is connected to pipette by tubing 26 and the pressure therein is monitored with a conventional pressure transducer 28 interfaced to a system computer 24 programmed to practice the present invention. Typical of pressure control 30 is a piston 34 connected with tubing 26 and the pipette 12 on a top side thereof, opposite pipette tip 20. Aspiration systems 10 like seen in FIG. 1 are well known to those skilled in the art and may be concocted with a variety of components and designs. Practicing the present invention requires only that pressure be used to cause liquid aspiration and dispensing from pipette 12 and that the aspiration pressure be monitored.

Liquid aspiration system 10 typically includes a transport device 22, indicated diagrammatically, which may be of any suitable type. The transport device 22 is capable of moving the pipette 12 laterally (the X-direction), vertically (the Z-direction) and from front to back (the Y-direction) in an analyzer to enable the pipette 12 to pick up a pipette tip 20 (when disposable tips are used), aspirate liquid 14 into the pipette tip 20 from a sample liquid reservoir 16 or tube 16 and to dispense a desired amount of sample liquid into a test assay element or other container (not shown). Generally, steppermotors, electronic drivers, interface circuits and limit-switches are used within transport device 22 to control transporting the pipette 12 and these are interfaced to system computer 24. Alternately, pipette 12 may be translated along the vertical z-axis by a rack-and-pinion drive. Conventional electronics are used to interface the transport device to the computer 24.

As shown, pipette 12 has a cavity 18 for holding liquid 14 and a tube 26 connected therefrom to a vacuum pressure measurement device or transducer 28 and to pressure control 30 for producing a variable vacuum pressure throughout the pipette 12 responsive to commands from computer 24. Such devices and sources are well known in the art. Commercially available pipettes 12 made from metals like stainless steel or plastics like polypropylene and similar materials, and tubing 26 made from vinyl, polypropylene, polyethylene, metal, etc., may used in the present invention. Pressure measurement device 28 measures air pressure within the pipette 12 both continuously and periodically during the aspiration method of the present invention. An exemplary pressure measurement device 28 is a pressure transducer for example, Model #26PCCFA2G from Honeywell) and is interfaced to the computer 24 to provide a measured air pressure within tubing 26 to computer 24.

An exemplary aspiration pressure control 30 is a piston-syringe device, mechanically connected to a stepper motor 34 and encoders or home limit-switches (not shown) capable of controlling the movement of the piston and causing pressure control 30 to aspirate and dispense air through tubing 26. Aspiration pressure control 30 and pressure sense device 28 are electronically interfaced to computer 24 which is used to control the operation of the liquid aspiration system 10. The computer 24 also provides signals to control the movement of the pipette 12 via transport device 22 as well as the aspiration into, and dispensing of liquid from, the pipette tip 24.

In such an instance, as illustrated in FIG. 1, pressure control 30 comprises a piston 34 attached to motor 32 for advancing and retracting the piston 34 within a closed chamber 36. A downward movement of piston 34 tends to increase the volume of the chamber 36, thereby to create vacuum or negative air pressure within the chamber 36 which draws air from the interconnected tubing 26, cavity 18, and pipette tip 20 into cavity 18 for aspirating liquid 14 into pipette tip 20. Advancing piston 34 into chamber 36 decreases the volume of chamber 36, thereby to provide a positive air pressure which pushes air out of chamber 36 into the interconnected tubing 26, cavity 18, and pipette tip 20 for expelling and dispensing liquid from the pipette tip 20 via the tip orifice. Thus, the piston 34 provides for aspiration of liquid into, and dispensing of liquid from, the pipette tip 20.

Tubing lengths and diameters of tubing 26 are selected to provide appropriate dynamic response of the pressure system to allow for proper level sensing and aspiration checking. The length of tubing 26 between the aspiration pressure control 30 and the pipette 12 provides a significant portion of the pressure head loss in the system 10, with the orifice at the end of pipette tip 20 providing most of the remaining pressure head loss. The length of tubing between the aspiration pressure control 30 and the pump provides sufficient pressure damping to reduce the pressure noise generating by the individual pump steps during operation of the pipette 12.

In accordance with the present invention, aspiration pressure control 30 and pressure sense device 28 are controlled and analyzed by computer 24 so as to determine the quality of the aspirated sample liquid 14 through analysis of a pressure profile generated during the aspiration process. The aspiration quality verification method has the ability to detect adverse events such as a full or partially clogged pipette tip 20. Herein, the term "proper aspiration" describes an aspiration free of such adverse events having a "proper profile" and the term "improper aspiration" describes an aspiration experiencing any of such adverse events and having an "improper profile". By providing the ability to detect other aspiration errors between the extremes of a fully clogged or fully open pipette tip 20, the present invention provides additional protection against supplying an analyzer with a liquid sample having clogs therein.

A key feature of the present invention is analyzing pressure measurements from pressure transducer 28 during a first predetermined period of time during the aspiration process, the first predetermined period of time beginning prior to the cessation of vacuum pressure applied by aspiration pressure control 30 to pipette tip 20. Aspiration pressure transducer 28 data are recorded throughout the entire aspiration process but only the pressure data gathered during the first predetermined period of time are used in making a clog detection analysis.

Figure 2:
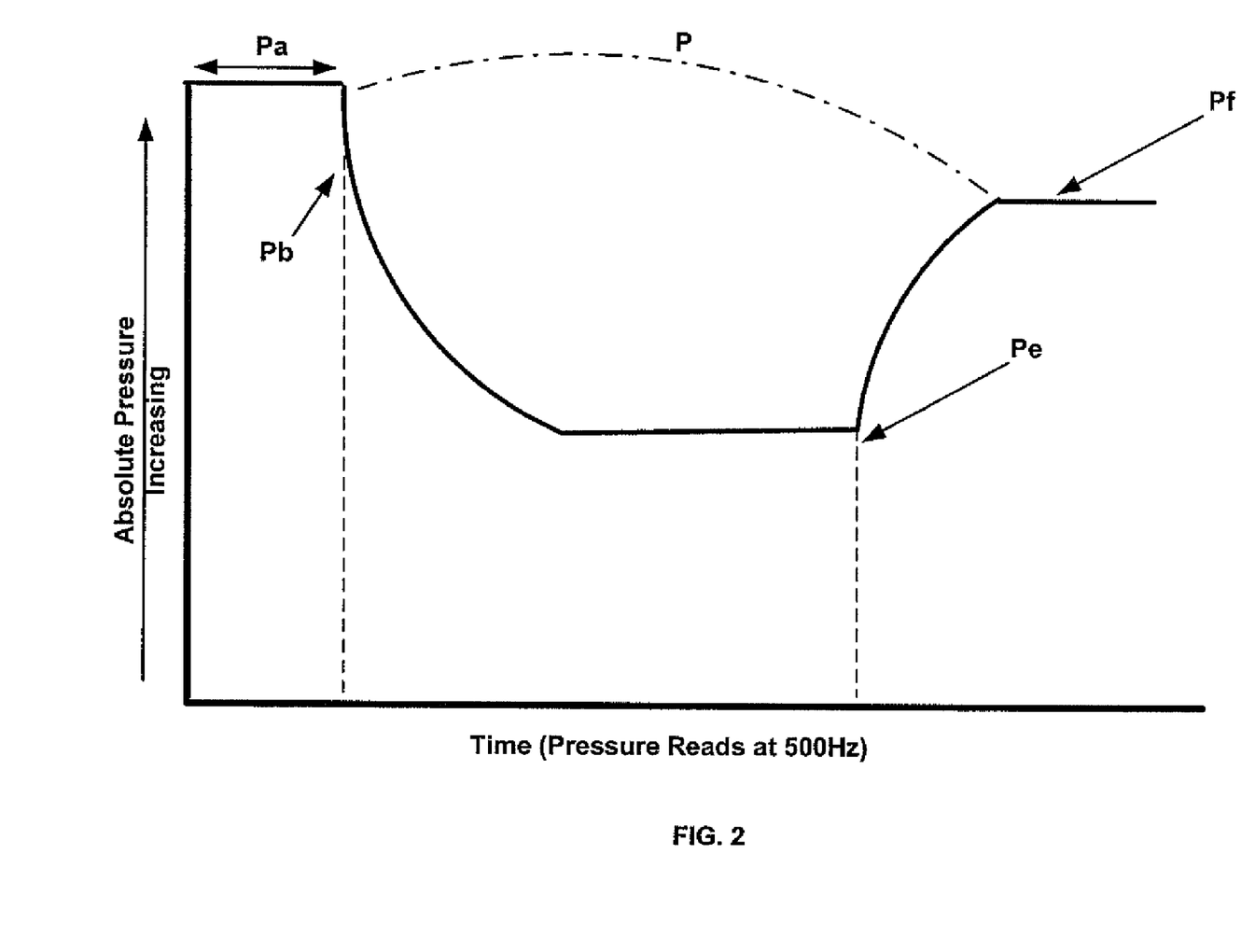
FIG. 2 is a graphical representation of a typical aspiration pressure profile obtained with the aspiration system of FIG. 1.

FIG. 2 illustrates a typical and well-known "proper aspiration pressure profile" descriptive of aspiration processes employing vacuum pressure provided by aspiration pressure control 30 and controlled by computer 24 to aspirate liquid 14 into pipette 12. Pressure data are collected in real time by pressure transducer 28 during the aspiration cycle, for instance using an AND (analog pressure signal converted to digital data) converter. In a typical embodiment, an analog input subsystem reads the pressure sense device at a constant rate (for example, 500 Hz) time stamping each reading and buffering the reading(s) for eventual inclusion into the aspiration data set. Prior to aspiration pressure control 30 being activated, ambient pressure Pa is measured by pressure transducer 28 for a specified interval of time to confirm that the ambient "zero-pressure" baseline is within a known normal range. Computer 24 activates aspiration pressure control 30 and liquid 14 is drawn into pipette 12 beginning with an initial aspiration pressure Pb and continuing during the full aspiration process indicated by the dash-dot line and identified as P in FIG. 2, the full aspiration process ending at a final pressure Pf.

During aspiration process P, and in accord with the present invention, clog detection data are gathered during a first predetermined period of time beginning prior to the ending of vacuum pressure indicated as Pe applied by aspiration pressure control 30 to pipette tip 20. The starting time for the first predetermined period of time Pe may be calculated and empirically confirmed based on the amount of liquid to be aspirated into pipette 12 and the characteristic vacuum profile of the combined aspiration pressure control 30, tubing 26 and pipette 12. This is a well-known determination involving the speed of movement of piston 34, the volume of chamber 36, size and length of interconnected tubing 26, and the dimension of cavity 18 and pipette tip 20. An exemplary amount of time during the first predetermined period of time Pe may be in the range of about 50 milliseconds and during Pe, an Average Aspiration Pressure AAPn of n vacuum pressure readings by pressure transducer 28 may be calculated by computer 24.

Figure 3:
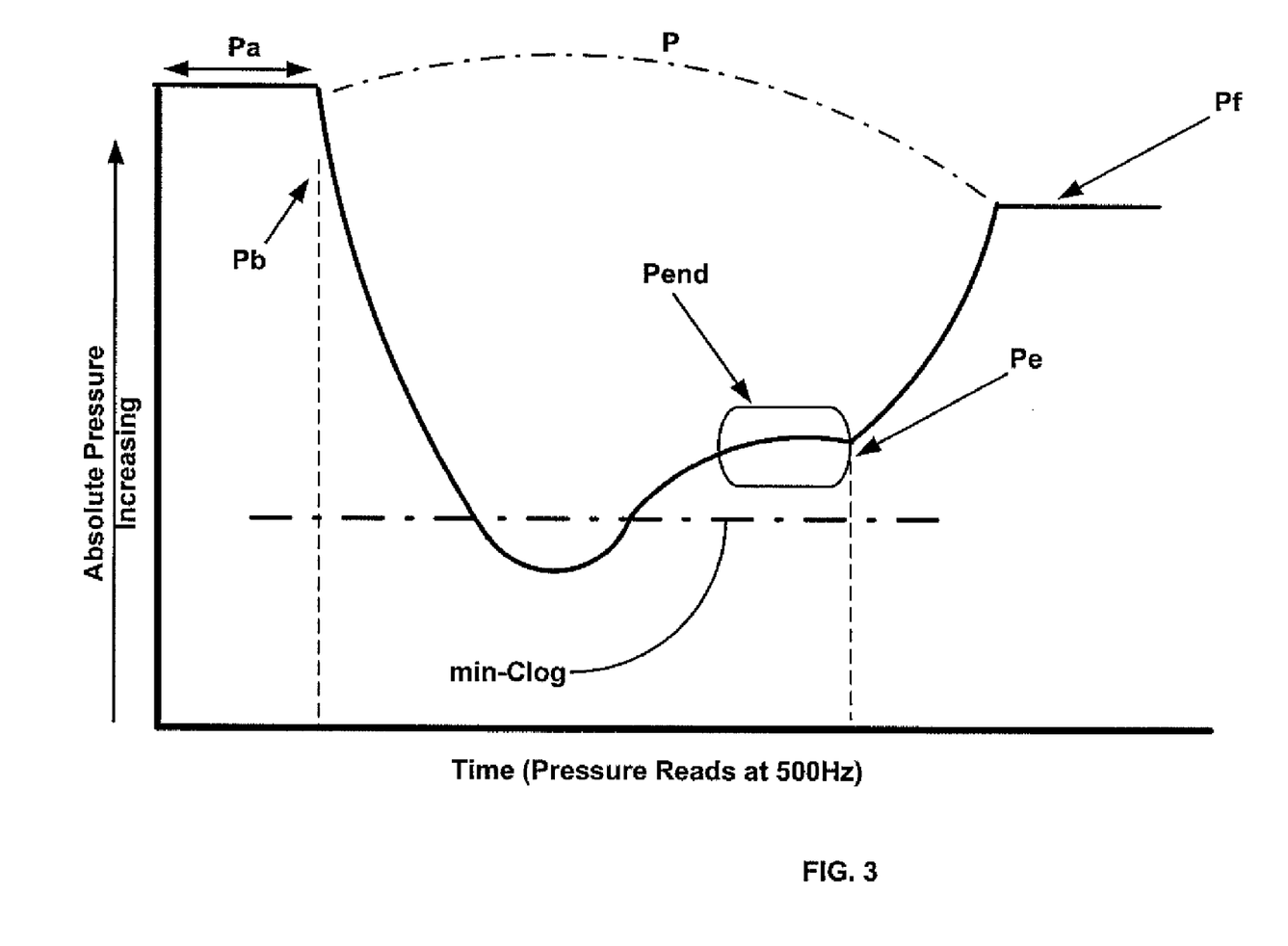
FIG. 3 is a graphical representation of an aspiration pressure profile obtainable with the aspiration system of FIG. 1 illustrating the absence of full or partial clogs.
Figure 4:
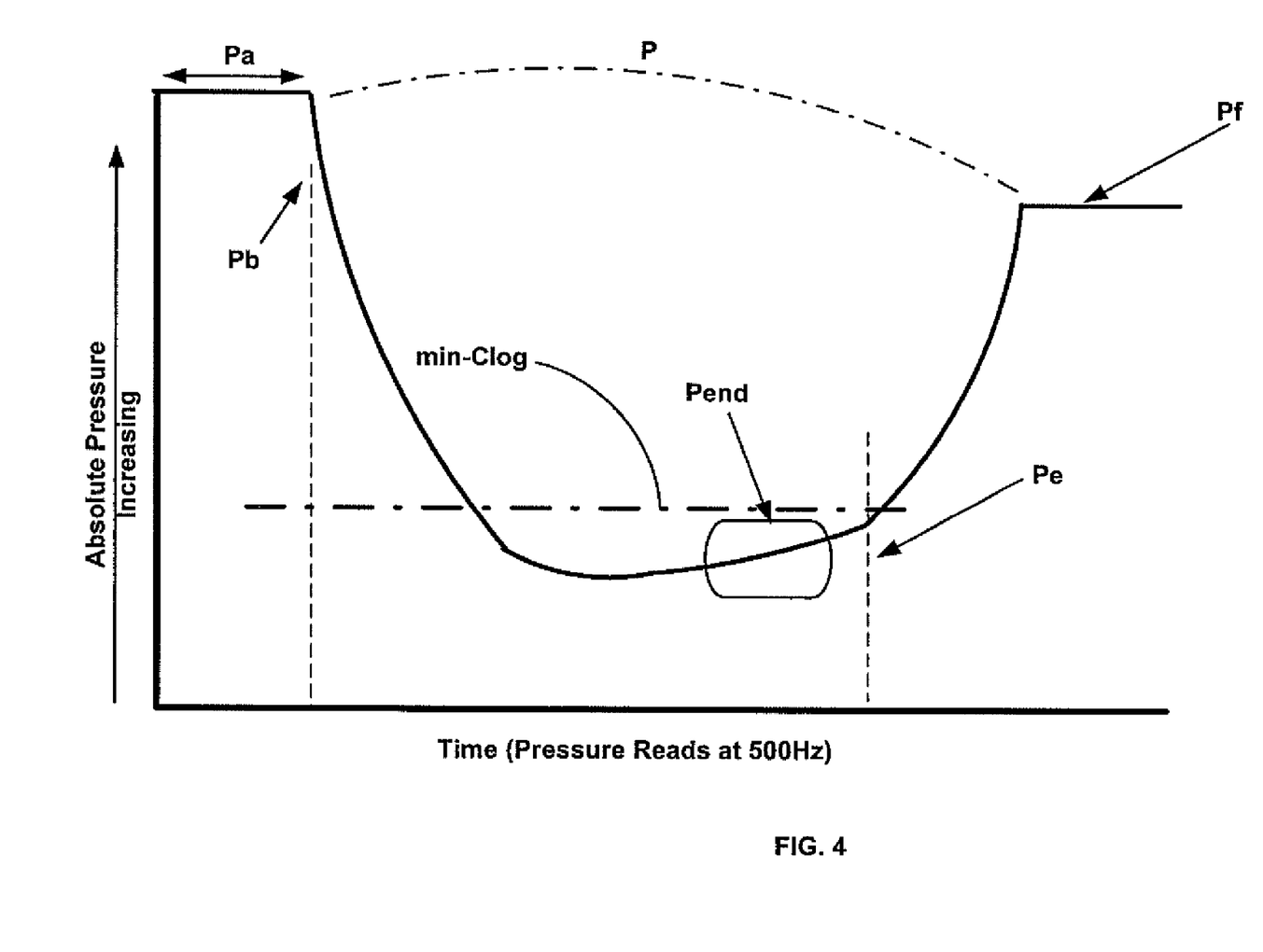
FIG. 4 is a graphical representation of an aspiration pressure profile obtainable with the aspiration system of FIG. 1 illustrating the presence of full or partial clogs.

Once Pn is determined, it is numerically compared to a min-CLOG threshold like illustrated in FIG. 3 in a dash-dotted line min-CLOG. The value of min-CLOG is empirically determined using liquids 14 known to contain clogs, for instance by doping liquid 14 with amounts of a gelatin substance. Min-CLOG will be different for different geometries of the components of liquid aspiration system 10, and is sensitive to the diameter of orifice of pipette tip 20 as well as to the particular characteristics of aspiration pressure control 30 and pipette 12. For example, in a system typically designed to aspirate sample volumes in the range of 2 micro-liters, first predetermined period of time indicated as Pe would be in the range of about 50 milliseconds and about ten n vacuum pressure readings would be recorded by transducer 28 at a pressure reading rate of about one reading every 5 milliseconds. During aspiration process P, if Pn is greater than min-CLOG, then it is determined that no clog occurred during aspiration process P. However, if Pn is less than min-CLOG, then it is determined that a clog has occurred during aspiration process P like illustrated in FIG. 4

Figure 5:
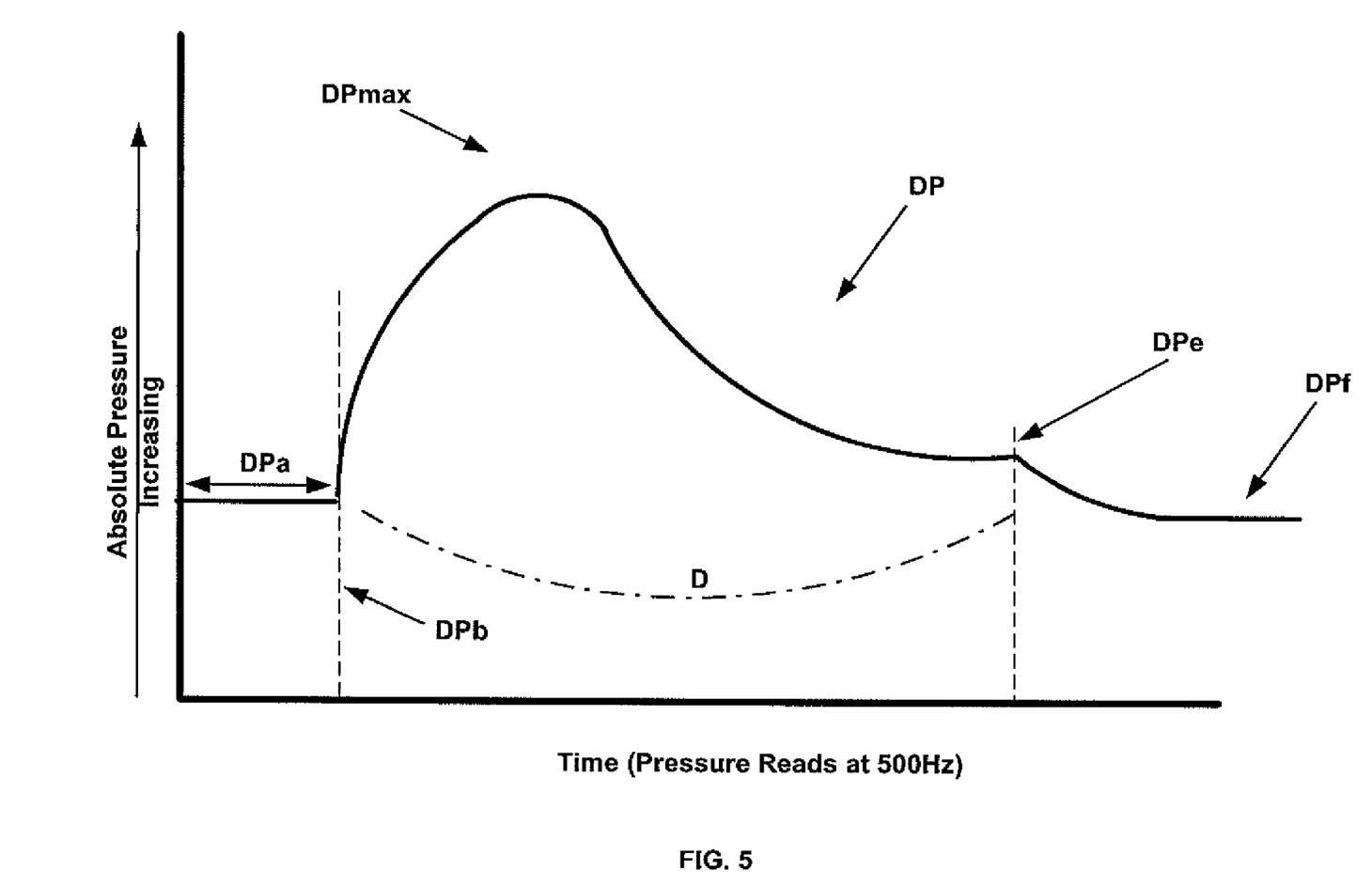
FIG. 5 is a graphical representation of a typical dispensing pressure profile obtained with the aspiration system of FIG. 1.
Figure 6:
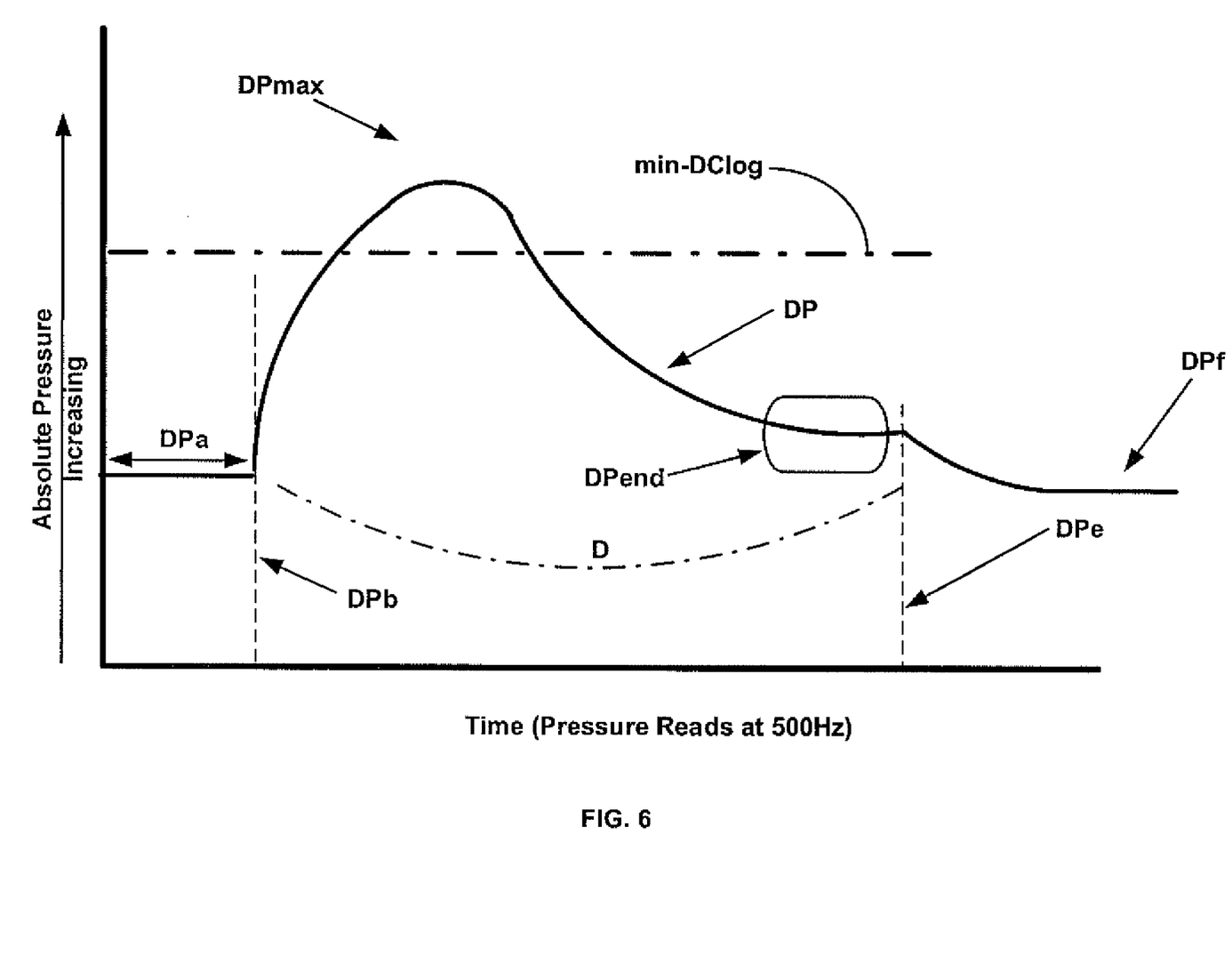
FIG. 6 is a graphical representation of an dispensing pressure profile obtainable with the aspiration system of FIG. 1 illustrating the absence of full or partial clogs.
Figure 7:
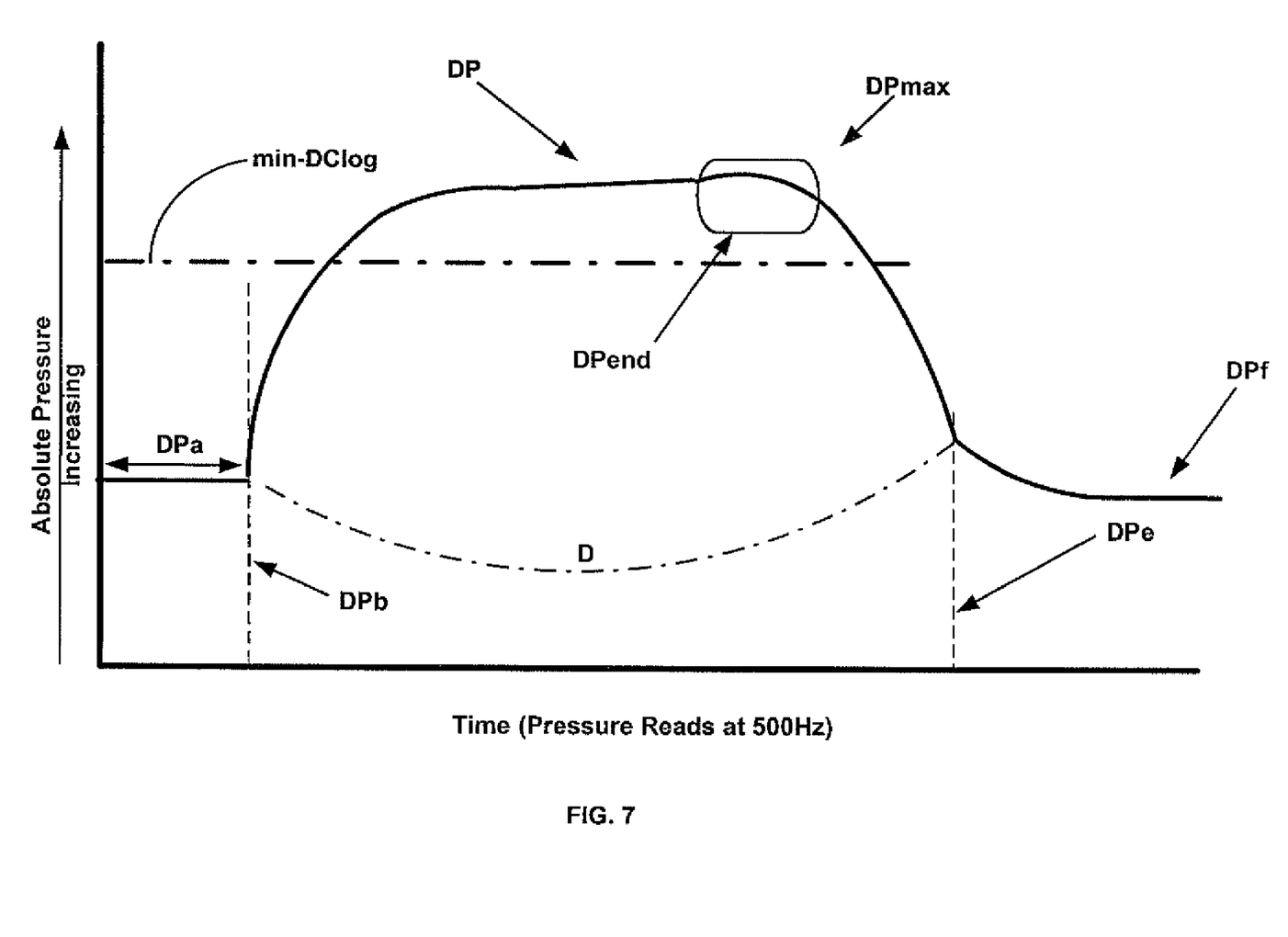
FIG. 7 is a graphical representation of an dispensing pressure profile obtainable with the aspiration system of FIG. 1 illustrating the presence of full or partial clogs.

Another feature of the present invention is a similar process like that described during aspiration of liquid 14 into pipette 12 but which takes place during dispensing of liquid 14 out of pipette 12 into another sample container, reagent container or reaction cuvette. FIG. 5 graphical representation of a typical dispensing pressure DP profile obtained with the aspiration system of FIG. 1. At the beginning of a dispensing process, dispensing pressure DP begins at a value slightly below ambient pressure DPa (in order to retain sample within pipette 12), climbs to a maximum dispensing pressure DPmax and slowly drops to a final dispensing pressure DPf. In accord with this feature of the present invention, as illustrated in FIG. 6, clog detection data are gathered during a second predetermined period of time indicated as Dpend beginning immediately prior to the cessation of positive vacuum pressure applied by aspiration pressure control 30 to fluid 14 previously aspirated into pipette 12 causing fluid 14 to dispense outwards through tip 20. The starting time for the second predetermined period of time DPend may be calculated in a similar manner as above and empirically confirmed based on the amount of liquid to be dispensed out of pipette 12. Again, an exemplary amount of time during the second predetermined period of time DPend may be in the range of about 50 milliseconds and during PDend, an average dispensing pressure ADPend of n vacuum pressure readings by pressure transducer 28 may be calculated by computer 24. Once ADPend is determined, it is numerically compared to a predetermined min-DCLOG threshold like illustrated in FIG. 6 in a dash-dotted line min-DCLOG. As previously described, the value of min-DCLOG is empirically determined using liquids 14 known to contain clogs, for instance by doping liquid 14 with amounts of a gelatin substance. In accord with the present invention it has been discovered that the average dispensing pressure ADPend measured during the second predetermined period of time DPend is less than the predetermined min-DCLOG, if and only if, the dispensing process was free of full or partial clogs, as illustrated in FIG. 6. If however, it is determined that the average dispensing pressure ADPend measured during the second predetermined period of time DPend exceeds the predetermined min-DCLOG, then the dispensing process is faulty because of the presence of full or partial clogs, as illustrated in FIG. 7.

Several techniques may be employed to reduce the impact of signal noise and other sources of imprecision on the determination of the presence of a pipette clog. For example, the median pressure may be calculated in place of the average pressure over the predetermined period of time. The median value is less sensitive than is the average value to individual outlier pressure measurements, such as those that may be caused by electrical noise. For example, over ten pressure measurements, a single outlier measurement value that is approximately twice as large as the other nine values will skew the average by 10%, but will have no effect on the median value. Another embodiment to improve detection robustness is to provide a small timing margin between the end of the predetermined measurement period and the end of the piston movement. Thus, if the system timing varies by a small amount as may occur in complex computer controlled mechanical systems, the pressure measurements will not include pressure values after the piston motion is complete and the pressure is shifting to its final value.

Those skilled in the art will appreciate that the embodiments of the invention disclosed herein are illustrative of the principles of the invention and that other modifications may be employed which are still within the scope of the invention. For example, variants of the invention should also be applicable to an air-coupled system with a few adjustments to the parameters. Another important variant of the present invention provides a method for analyzing aspiration pressure profiles to distinguish between fluid types; for example, normal serum from whole blood or liquid from air. In particular, proper operation of analyzer 10 may be enhanced by differentiating liquid from air, for example, to verify the presence (or absence) of liquid in a liquid drain to check drain functionality or to verify that probe cleaner present in a probe cleaner port during a probe cleansing process.

Figure 8:
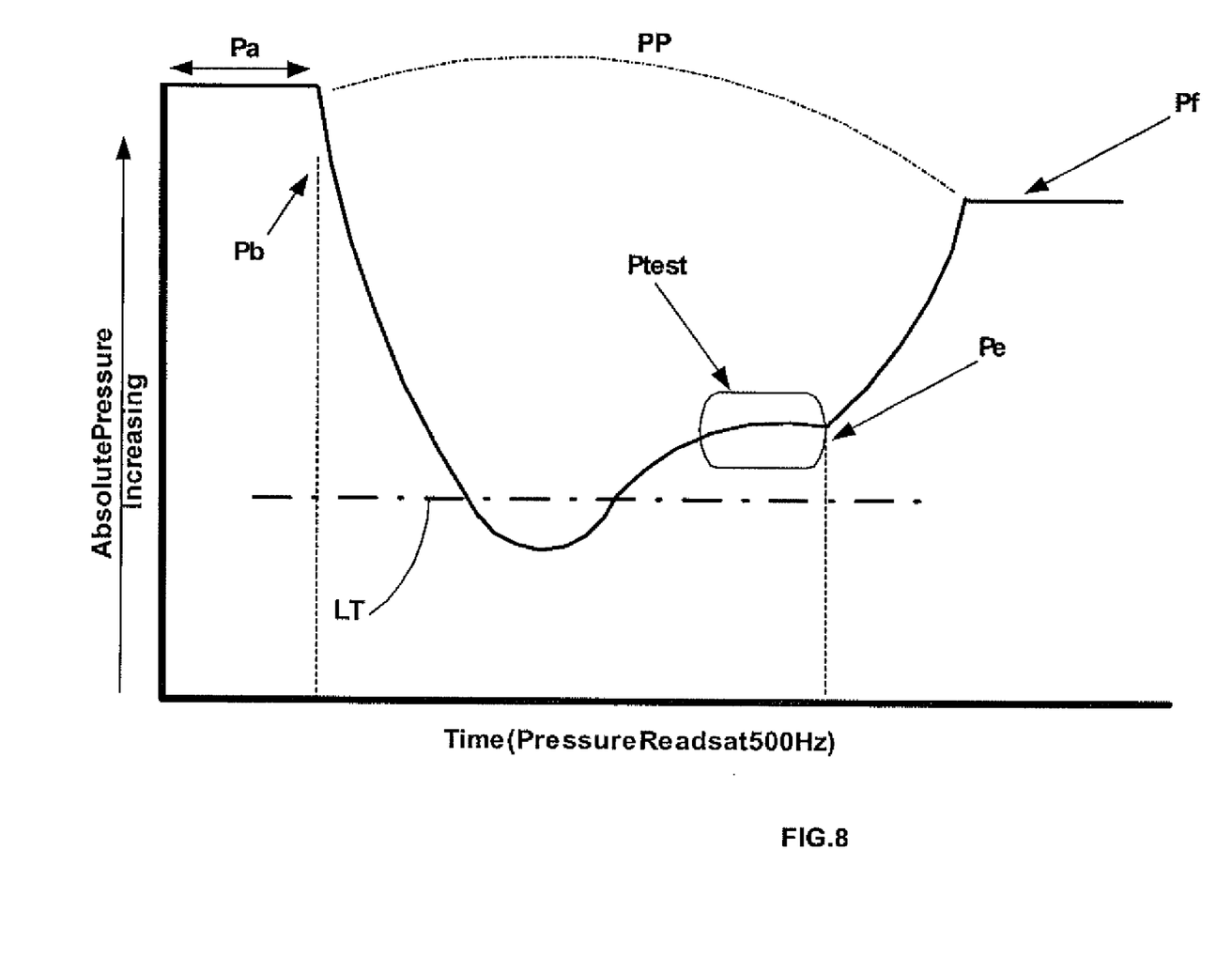
FIG. 8 is a graphical representation of an aspiration pressure profile obtainable with the aspiration system of FIG. 1 illustrating the aspiration of air; and, FIG. 9 is a graphical representation of an aspiration pressure profile obtainable with the aspiration system of FIG. 1 illustrating the aspiration of liquid.
Figure 9:
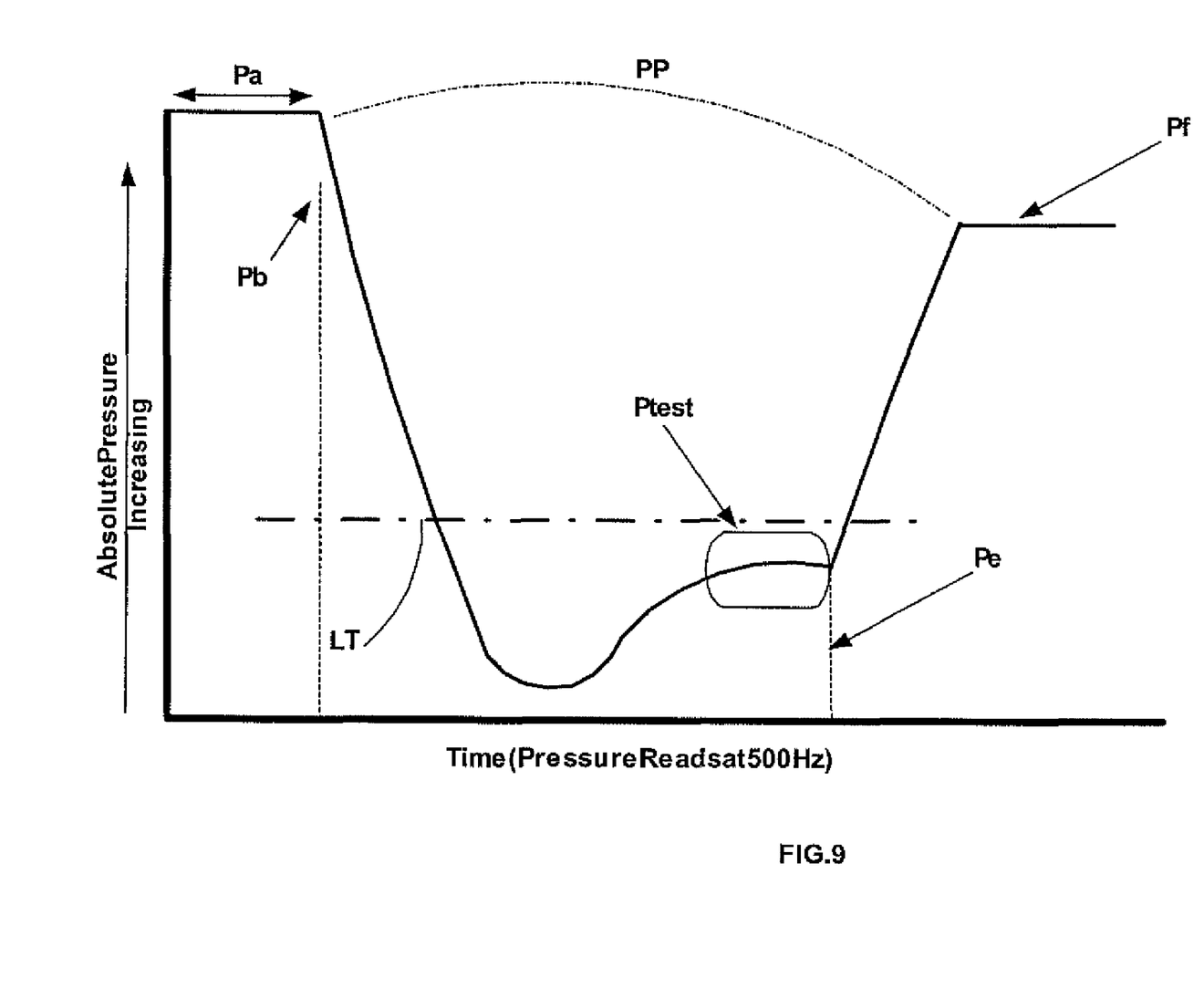

To perform the liquid presence verification test of the present invention, a liquid threshold LT is determined by aspirating an predefined first amount of air at ambient Pa into pipette 12, and for improved accuracy, defining the liquid threshold LT at a predetermined level below the measured ambient pressure Pa. Next, the test substance is aspirated into pipette 12 and pressure within pipette 12 PP is measured, as seen in FIG. 8, during a brief period of time Ptest. It has been discovered that if the measured pressure PP is greater than the newly established liquid threshold LT then pipette 12 is known to have aspirated air, like seen in FIG. 8. In contrast, if the measured pressure PP is greater than the newly established liquid threshold LT, like illustrated in FIG. 9, it has been discovered that pipette 12 has aspirated liquid.

Accordingly, the present invention is not limited to those embodiments precisely shown and described in the specification but only by the following claims.

What is claimed is:

1. A method for determining the presence of a clogged pipette during aspiration of liquid from a container into said pipette, said method comprising the steps of:
    determining an aspiration pressure curve representative of pressure within the pipette;
    analyzing the aspiration pressure curve only during a period of time beginning about 50 milliseconds prior to the end of the aspiration process and ending at the end of the end of the aspiration process;
    calculating a pressure related variable during said period of time; and
    comparing said pressure related variable to a predetermined value, wherein the predetermined value is selected such that said pipette is free of clogs only if said pressure related variable is greater than said predetermined value.

2. The method of claim 1 wherein calculating a pressure related variable comprises calculating an average pressure reading.

3. The method of claim 1 wherein calculating a pressure related variable comprises calculating a median pressure reading.

4. A method for determining the presence of a clogged pipette during dispensing of liquid from said pipette into a container, said method comprising the steps of:
    determining a dispensing pressure curve representative of pressure within the pipette;
    analyzing the dispensing pressure curve only during a period of time beginning about 50 milliseconds prior to the end of the dispensing process and ending at the end of the end of the dispensing process;
    calculating a pressure related variable during said period of time; and,
    comparing said pressure related variable to a predetermined value, wherein the predetermined value is selected such that said pipette is free of clogs only if said pressure reading does not exceed said predetermined value.

5. The method of claim 4 wherein calculating a pressure related variable comprises calculating an average pressure reading.

6. The method of claim 4 wherein calculating a pressure related variable comprises calculating a median pressure reading.

7. A method for differentiating fluid types aspirated between a container and a pipette, said method comprising:
- determining an aspiration pressure curve representative of pressure within the pipette;
- analyzing the aspiration pressure curve only during a period of time beginning about 50 milliseconds prior to the end of the aspiration process and ending at the end of the end of the aspiration process;
- calculating a pressure related variable during said period of time; and
- comparing said pressure related variable to a predetermined value, wherein the predetermined value is selected such that said fluid types are differentiated based on whether said pressure reading is above or below said predetermined value.

8. The method of claim 7 wherein calculating a pressure related variable comprises calculating an average pressure reading.

9. The method of claim 7 wherein calculating a pressure related variable comprises calculating a median pressure reading.

10. The method of claim 7 wherein said fluid types comprise liquid and air.

* * * * *